(12) United States Patent
Hamada et al.

(10) Patent No.: US 7,145,030 B2
(45) Date of Patent: Dec. 5, 2006

(54) PRODUCTION METHOD FOR OPTICALLY ACTIVE N-ARYL-β-AMINO ACID COMPOUNDS

(75) Inventors: Takayuki Hamada, Kawasaki (JP); Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 90 days.

(21) Appl. No.: 10/826,374

(22) Filed: Apr. 19, 2004

(65) Prior Publication Data

US 2004/0267043 A1 Dec. 30, 2004

(30) Foreign Application Priority Data

Apr. 24, 2003 (JP) ............................. 2003-119327

(51) Int. Cl.
*C07C 229/00* (2006.01)

(52) U.S. Cl. ...................................................... 560/43

(58) Field of Classification Search ...................... None
See application file for complete search history.

(56) References Cited

OTHER PUBLICATIONS

Lemieux et al, Canadian Journal of Chemistry, Biochemistry of the Ustiliginales. IV. The Configuration of Some beta-Hydroxyacids and the Bioreduction of beta-Ketoacids 1951, 37(11), pp. 678-690.
F. Effenberger, et al., Liebigs Annalen der Chemie, No. 2, XP-000946460, pp. 314-333, "Enantioselektive Synthese N-Substituierter α-Aminocarbonsäuren Aus α-Hydroxycarbonsäuren", 1986 (with English Abstract).
D. Seebach, et al., Tetrahedron Letters, vol. 28, No. 27, XP-002023609, pp. 3103-3106, "α-Alkylation of β-Aminobutanoates With IK-1.2-Induction", 1987.
S.Y. Dike, et al., Synlett, vol. 6, XP-002290034, pp. 443-444, "A New Chemoenzymatic Enantioselective Synthesis of Optically Active Benzothiopyran and Benzothiazepin Ring System", Jun. 1991.
J.-I. Sakaki, et al., Chem. Pharm. Bull., vol. 37, No. 11, XP-002290035, pp. 2952-2960, "Synthesis of 1,3-Dioxin-4-Ones and Their Use in Synthesis. XVIII. Synthesis of Azetidin-2-Ones From 1,3-Dioxin-4-Ones Via 3-Hydroxycarboxamides", 1989.
S. Dakoji, et al., Bioorganic and Medicinal Chemistry, vol. 5, No. 12, XP-002290036, pp. 2157-2164, "Redesigning the Active-Site of an Acyl-CoA Dehydrogenase: New Evidence Supporting a One-Base Mechanism", 1997.
H. Urata, et al., Tetrahedron Letters, vol. 32, No. 26, XP-002290037, pp. 3091-3094, "Carbonylation of Alkyl Sulfonates Catalyzed by Cobalt Complexes", 1991.
D. Ma, et al., Organic Letters, vol. 3, No. 16, XP-002290038, pp. 2583-2586, "CUL-Catalyzed Coupling Reaction of β-Amino Acids or Esters with Aryl Halides at Temperature Lower Than That Empolyed in the Normal Ullmann Reaction. Facile Synthesis of SB-214857", Aug. 9, 2001.
O. Banjoko, et al., "Kinetics of the Reactions of Phenyl 2,4,6-Trinitrophenyl Ether With Piperidine, N-Butylamine, Aniline, Benzylamine, and Morpholine in Benzene", J. Chem. Soc. Perkin II, 1981, pp. 1105-1107.
D. Ma, et al., "CuI-Catalyzed Coupling Reaction of Beta-Amino Acids or Esters with Aryl Halides at Temperature Lower Than That Empolyed in the Normal Ullmann Reaction. Facile Synthesis of SB-214857", Organic Letters, vol. 3, No. 16, 2001, pp. 2583-2586.
S.G. Davies, et al., "Asymmetric Synthesis of R-Beta-Amino Butanoic Acid and S-Beta-Tyrosine: Homochiral Lithium Amide Equivalents For Michael Additions to Alpha, Beta-Unsaturated Esters", Tetrahedron: Asymmetry, vol. 2, No. 3, 1991, pp. 183-186.

*Primary Examiner*—Paul A. Zucker
(74) *Attorney, Agent, or Firm*—Oblon, Spivak, McClelland, Maier & Neustadt, P.C.

(57) ABSTRACT

The present invention provides an effective method for the production of optically active N-aryl-β-amino acid compounds, which at the same time is suitable for industrial production. In the method of the present invention optically active sulfonylated β-hydroxycarboxylic acid compounds, which are readily derived from β-keto carboxylic acid compounds, are reacted with aromatic amines to produce optically active N-aryl-β-amino acid compounds.

18 Claims, No Drawings

PRODUCTION METHOD FOR OPTICALLY ACTIVE N-ARYL-β-AMINO ACID COMPOUNDS

TECHNICAL FIELD

The present invention relates to a production method for optically active N-aryl-β-amino acid compounds useful as intermediate compounds for pharmaceuticals and agrochemicals etc.

BACKGROUND ART

Optically active N-aryl-β-amino acid compounds are important intermediate compounds etc. for pharmaceuticals as shown in Organic Letters, 2001, 3, 2585 to 2586.

As a production method for optically active N-aryl-β-amino acid compounds, for instance, a process involving diastereoselective reduction of N-aryl-β-dehydroamino acid menthyl ester is described in J. Org. Chem., 2002, 67, 4667 to 4679. However, a stoichiometric amount of L-menthol is required for this method. Moreover, several additional processes such as derivatization into the N-aryl-β-dehydroamino acid menthyl ester and final hydrolysis to obtain the desired compounds are necessary. In addition to this disadvantage, the ee (enantiomeric excess) of the N-aryl-β-amino acid compound obtained by this method is less than 60% and only the (S) isomer is prepared from the natural menthol ester and therefore the (R) isomer cannot be synthesized economically.

A process using a Reformatzky-type asymmetric addition reaction with aldimines as starting materials (Chemical Letters, 2001, (3), 254~255) and a process using an asymmetric Mannich reaction (Tetrahedron, 2001, 57, 875~877) were reported as other methods. However, in the case of the Reformatzky method, a hydroxy group is essential in the ortho-position of the aniline of the aldimine, and therefore the manufacturing of N-aryl-β-amino acids having no hydroxy group in 2-position of the phenyl group is not possible. The Mannich method requires a stoichiometric amount of acetates with axial chirality. Since the preparation of acetates with axial chirality is not easy, this is unlikely to be an economically superior method. For these reasons, neither method is a satisfactory process for industrial production.

A copper catalyzed coupling reaction using β-amino acids and aryl halides was also described (Organic Letters, 2001, 3 (16), 2585 to 2586). However, there is an environmental problem for this process considering about the issue of copper waste treatment. Furthermore, β-amino acids are not so readily available in commercial quantities. There are several synthetic methods to produce β-amino acids using inexpensive β-keto carboxylic acid compounds as starting materials, which include a method by azidaion of β-hydroxycarboxylic acid esters using the Mitsunobu reaction (Synlett, 1998, 11, 1189 to 1190) and a process by the substitution reaction of sulfonylated β-hydroxycarboxylic acid esters with azide or benzylamine followed by reduction (Tetrahedron Letters, 1987, 28, 3103 to 3106). However, these processes require rather longer reaction sequences such as asymmetric reduction of β-keto carboxylic acid compounds, sulfonylation, reaction with azide or benzylamine, hydrogenation with metal catalysts and arylation process with copper. Consequently, a method using the copper catalysts described above cannot be regarded as an industrially suitable process.

DISCLOSURE OF THE INVENTION

[Problems to be Solved by the Invention]

Regarding the background of the prior art in the preceding description, the purpose of the present invention is to provide an effective production method for N-aryl-β-amino acid compounds, which is at the same time suitable for industrial production.

[Means for Solving the Problems]

Following the detailed investigation of how to solve the above mentioned problems, the inventors have found that the reaction of the optically active sulfonylated β-hydroxycarboxylic acid compounds, which are easily derived from inexpensive β-keto carboxylic acid compounds, with aromatic amines can produce the optically active N-aryl-β-amino acid compounds in high yield with high optical purity, and the results brought the present invention to completion.

Previously, a method for the synthesis of optically active N-aryl-α-amino acids by the reaction of trifluoromethylsulfonyl compounds of optically active α-hydroxycarboxylic acids with aromatic amines has been reported (Liebigs Annalen der Chemie, 1986, (2), 314~333). However, the reaction of sulfonylated compounds of optically active β-hydroxycarboxylic acid compounds with aromatic amines has not been reported at all. On the other hand, it has been known that an elimination reaction of sulfonylated β-hydroxycarboxylic acids compounds takes place to generate α,β-unsaturated carboxylic acid compounds in the presence of bases such as triethylamine, DBU or ammonium hydroxide (Synthesis, 1986, (3), 184 to 189). On the contrary, in the case of aminations of sulfonylated α-hydroxycarboxylic acids, such an elimination reaction is unlikely to take place to form α,β-unsaturated carboxylic acid compounds.

The present inventors found that regardless of the conditions for facile elimination and addition leading to eventual epimerization, the reaction of sulfonylated β-hydroxycarboxylic acid compounds with aromatic amines successfully afforded the optically active N-aryl-β-amino acids with high optical purity in high yield. It is also well known that optically active β-hydroxycarboxylic acid compounds having the desired configuration can be obtained in high yield with high optical purity by asymmetric reduction of inexpensive β-keto carboxylic acids. The present inventors found that a superior production method for the optically active N-aryl-β-amino acids was developed by combining the amination described above with an asymmetric reduction and sulfonylation.

The present invention thus comprises the following;

[1] A production method characterized in that optically active sulfonate compounds represented by the following general formula (1)

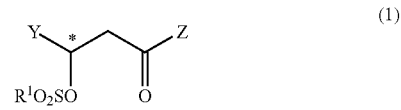

are reacted with an aromatic amine represented by the following formula (2)

resulting in the optically active N-aryl-β-amino acid compounds represented by the following formula (3).

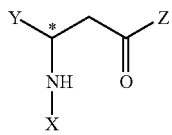

(3)

[2] A production method as set out in [1] comprising a process, in which by the reaction of optically active β-hydroxycarboxylic acid compounds represented by the following formula (5)

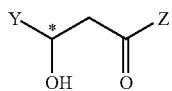

(5)

with sulfonyl chlorides or sulfonic acid anhydrides, the optically active sulfonate compounds represented by the above described formula (1) are manufactured.

[3] A production method as set out in [2] comprising a process, in which by the asymmetric reduction of β-keto carboxylic acid compounds represented by the following formula (4)

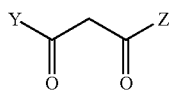

(4)

in the presence of a catalyst, optically active β-hydroxycarboxylic acid compounds represented by the above described formula (5) are manufactured.

[4] production method for optically active N-aryl-β-amino acid compounds as set out in any of [1] to [3] characterized in that $R^1$ in the sulfonyl compounds, represented by the above described formula (1), is a trifluoromethyl, methyl or p-tolyl group.

[5] A production method for optically active N-aryl-β-amino acid compounds as set out in [4] characterized in that $R^1$ in the sulfonyl compounds, represented by the above described formula (1), is trifluoromethyl.

[6] A production method for optically active N-aryl-β-amino acid compounds as set out in any of [1] to [5] characterized in that in the sulfonate compounds, represented by the above described formula (1), the relevant sulfonyl group is introduced by using trifluoromethanesulfonic acid anhydride as sulfonylation agent and that $R^1$ is a trifluoromethyl group.

[7] A production method for optically active N-aryl-β-amino acid compounds as set out in any of [1] to [6] characterized in that the relevant reaction is carried out at a temperature of 5° C. and less.

BEST MODE FOR CARRYING OUT THE INVENTION

In the following the present invention is explained in detail.

According to the present invention, Y represents an optionally substituted methyl or aryl group in the formula. If the methyl group is substituted, there is no special limitation on the substituent provided that it does not hinder the reaction for the present invention, and the number of substituents is selected from a range from 1 to 3. In case that it has multiple substituents, these may be each identical substituents, or each may be a different substituent or they may be taken together to form a ring.

As examples for the substituent where Y has substituents, may be mentioned alkyl groups such as methyl group, ethyl group, n-propyl group, isopropyl group, n-butyl group, isobutyl group, sec-butyl group, tert-butyl group etc.; aralkyl groups such as benzyl group etc.; cycloalkyl groups such as cyclopropyl group, cyclobutyl group, cyclopentyl group, cyclohexyl group etc.; alkoxy groups such as methoxy group, ethoxy group, n-propoxy group, isopropoxy group, n-butoxy group, tert-butoxy group, benzyloxy group etc.; acyloxy groups such as acetoxy group, benzoyloxy group etc.; alkylthio groups such as methylthio group, ethylthio group, n-propylthio group, isopropylthio group, n-butylthio group, tert-butylthio group, benzylthio group etc.; acylthio groups such as the acetylthio group, benzoylthio group etc.; hydroxy group, halogen atoms such as fluorine chlorine, bromine, iodine etc.; carboxylic acid, sodium carboxylic acid; sulfonic acid, sodium sulfonic acid; vinyl group, allyl group; aryl groups such as phenyl group, naphthyl group, furyl group, thienyl group, indolyl group, pyridyl group etc.; carbonyl groups such as formyl group, acetyl group, trifluoroacetyl group, benzoyl group, methoxycarbonyl group, ethoxycarbonyl group, tert-butoxycarbonyl group, vinyloxycarbonyl group, allyloxycarbonyl group, benzyloxycarbonyl group, methylaminocarbonyl group etc.; sulfonyl groups such as alkylsulfonyl group, arylsulfonyl group, sulfonamido group etc.; amino group; primary amino groups such as N-methylamino group, N-ethylamino group, N-n-propylamino group, N-isopropylamino group, N-n-butylamino group, N-isobutylamino group, N-benzylamino group, N-methoxycarbonylamino group, N-tert-butoxycarbonylamino group, N-benzyloxycarbonylamino group, N-phenylamino group, N-mesylamino group, N-tosylamino group, formylamino group etc.; secondary amino groups such as N,N-dimethylamino group, N,N-diethylamino group, N,N-dibenzylamino group, N-ethyl-N-methylamino group, N,N-di-n-propylamino group, N,N-di-isopropylamino group, N,N-di-n-butylamino group, N,N-diisobutylamino group, N-methyl-N-phenylamino group, N-benzyl-N-methylamino group, N-mesyl-N-methylamino group, piperidyl group, pyrrolidyl group etc.; nitroso group; cyano group; halomethyl groups such as monochloromethyl group, difluoromethyl group, trifluoromethyl group, trichloromethyl group, pentafluoromethyl group etc.; haloaryl groups such as monofluorophenyl group, trifluorophenyl group, pentafluorophenyl group etc.

According to the present invention, Z stands for a hydroxy group, an optionally substituted amino group, an optionally substituted alkoxy group or an optionally substituted aryloxy group in the formula. If the groups are substituted, there is no special limitation on the substituent provided that it should not hinder the reaction, and the groups may also have multiple substituents. In the case that they have multiple substituents, these may be each identical substituents or each may be a different substituent.

As examples of substituents on Z, methyl group, ethyl group, n-propyl group, isopropyl group, n-butyl group, isobutyl group, sec-butyl group, tert-butyl group, benzyloxycarbonyl group, phenyl group, mesyl group, tosyl group, formyl group etc. may be mentioned in the case of substituents on the amino group. Moreover ethyl group, ethyl group, n-propyl group, isopropyl group, n-butyl group, isobutyl group, sec-butyl group, tert-butyl group, benzyl group, pyridyl group, cyclopropyl group, cyclobutyl group, cyclopentyl group, cyclohexyl group, L-menthyl group, vinyl group, allyl group etc. may be mentioned in the case of substituents on the alkoxyl group and phenyl group, p-tolyl group, p-nitrophenyl, naphthyl group etc. may be mentioned in the case of substituents on the aryloxy group.

As optionally substituted amino groups, there may be mentioned for example the following; N-methylamino group, N-ethylamino group, N-n-propylamino group, N-isopropylamino group, N-n-butylamino group, N-isobutylamino group, N-benzylamino group, N-methoxycarbonylamino group, N-tert-butoxycarbonylamino group, N-benzyloxycarbonylamino group, N-phenylamino group, N-mesylamino group, N-tosylamino group, formylamino group, N,N-dimethylamino group, N,N-diethylamino group, N,N-dibenzylamino group, N-ethyl-N-methylamino group, N,N,-di-n-propylamino group, N,N-di-isopropylamino group, N,N-di-n-butylamino group, N,N,-diisobutylamino group, N-methyl-N-phenylamino group, N-benzyl-N-methylamino group, N-mesyl-N-methylamino group, piperidyl group, pyrrolidyl group, etc.

As optionally substituted alkoxy groups, there may be mentioned for example the following methoxy group, ethoxy group, n-propoxy group, isopropoxy group, n-butoxy group, isobutoxy group, sec-butoxy group, tert-butoxy group, benzyloxy group, pyridyloxy group; cyclopropoxy group, cyclobutoxy group, cyclopentyloxy group, cyclohexyloxy group, L-menthyloxy group, vinyloxy group, allyloxy group etc.

As optionally substituted aryloxy groups there may be mentioned the phenoxy group, p-tolyloxy group, p-nitrophenyloxy group, naphthyloxy group, etc.

In the formula according to the present invention, $R^1$ represents an optionally substituted alkyl group with a carbon atom number from 1 to 10, an optionally substituted aryl group with a carbon atom number from 6 to 15, an optionally substituted aralkyl group with a carbon atom number from 7 to 20. If the groups are substituted, there is no special limitation on the substituent provided that it does not hinder the reaction for the present invention, and they may also have multiple substituents. In case that they have multiple substituents, these may be each identical substituents or each may be a different substituent.

As examples of substituents on $R^1$, hydrogen atom, fluorine atom, chlorine atom, bromine atom, iodine atom, hydroxyl group, amino group, nitro group, nitroso group, cyano group etc. may be mentioned.

As optionally substituted alkyl groups with a carbon atom number from 1 to 10, there may be mentioned the methyl group, ethyl group, n-propyl group, isopropyl group, n-butyl group, isobutyl group, sec-butyl group, tert-butyl group, cyclopropyl group, cyclobutyl group, cyclopentyl group, cyclohexyl group, L-menthyl group, monochloromethyl group, difluoromethyl group, trifluoromethyl group, trichloromethyl group, pentafluoroethyl group etc.

As optionally substituted aryl groups with a carbon atom number from 6 to 15, there may be mentioned the phenyl group, tolyl group, naphthyl group, monofluorophenyl group, trifluorophenyl group, pentafluorophenyl group etc.

As optionally substituted aralkyl groups with a carbon atom number from 7 to 20, there may be mentioned the benzyl group, phenethyl group etc.

In the formula according to the present invention, X stands for an optionally substituted aryl group with a carbon atom number from 6 to 15 or an optionally substituted heteroaromatic group with a carbon atom number from 3 to 15. As aryl groups with a carbon atom number from 6 to 15 the phenyl group, naphthyl group etc. may be mentioned. As heteroaromatic groups with a carbon atom number from 3 to 15, the furyl group, thienyl group, pyrrolyl group, pyridyl group etc. may be mentioned.

If the groups are substituted, there is no special limitation on the substituent provided that it should not hinder the reaction for the present invention, and they may also have multiple substituents. In case that they have multiple substituents, these may be each identical substituents or each may be a different substituent. As examples for substituents on X, the same substituents as for Y may be mentioned.

As the preferred situation for the optically active sulfonate compounds represented by the formula (1) and the optically active N-aryl-β-amino acid compounds represented by the formula (3) for instance, the optically active sulfonate compounds represented by the formula (1') and the optically active N-aryl-β-amino acid compounds represented by the formula (3') may be mentioned.

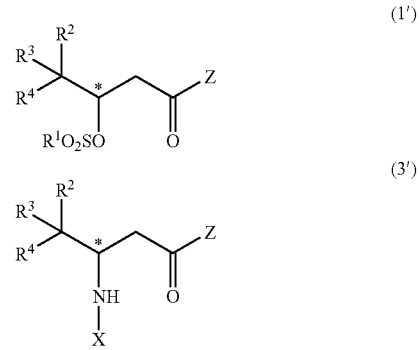

In the formula (1') and (3') X, Z and $R^1$ have the same meaning as described above. * indicates an optically active carbon atom in the R or S configuration. $R^2$, $R^3$ and $R^4$ each independently stand for a hydrogen atom or an optionally substituted alkyl group with a carbon atom number from 1 to 10, an optionally substituted aryl group with a carbon atom number from 6 to 15, an optionally substituted aralkyl group with a carbon atom number from 7 to 20. If the groups are substituted there is no special limitation on the substituent provided that it should not hinder the reaction for the present invention, and they may also have multiple substituents. In case that they have multiple substituents, these may be each identical substituents or each may be a different substituent.

As optionally substituted alkyl groups with a carbon atom number from 1 to 10, there may be mentioned the methyl group, ethyl group, n-propyl group, isopropyl group, n-butyl group, isobutyl group, sec-butyl group, tert-butyl group, cyclopropyl group, cyclobutyl group, cyclopentyl group, cyclohexyl group, L-menthyl group, monochloromethyl group, difluoromethyl group, trifluoromethyl group, trichloromethyl group, pentafluoroethyl group etc.

As optionally substituted aryl groups with a carbon atom number from 6 to 15, there may be mentioned the phenyl group, tolyl group, naphthyl group, monofluorophenyl group, trifluorophenyl group, pentafluorophenyl group etc.

As optionally substituted aralkyl groups with a carbon atom number from 7 to 20, there may be mentioned the benzyl group, phenethyl group etc.

The optically active sulfonate compounds (1) for the present invention may be prepared by the asymmetric reduction of β-keto carboxylic acid compounds represented by the following formula (4) and ensuing sulfonylation of the obtained optically active β-hydroxycarboxylic acid compounds represented by the following formula (5).

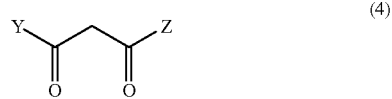

(4)

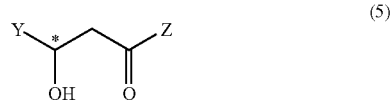

(5)

For instance, β-keto carboxylic acid compounds represented by the formula (4), which may be prepared according to a method published in J. Am. Chem. Soc., 1987, 109, 5856 to 5858, are transformed quantitatively into the optically active β-hydroxycarboxylic acid compounds represented by the formula (5) by asymmetric reduction for instance in the presence of a small quantity (e.g. in a range of 0.05%) of Ru-binap catalyst ($RuCl_2$, (R)-binap, $RuCl_2$, (S)-binap etc.) with high optical purity and these may be cheaply manufactured. Further, by selecting the catalyst, the (R) or (S) configuration respectively may be obtained as desired for the configuration of the optically active carbon atom of formula (4). Moreover, β-keto carboxylic acid with >99% ee compounds may be prepared in microbial method, reported in Journal of Molecular Catalysis B: Enzymatic (1998), 5(1–4), 129–132, or in Journal of Organic Chemistry (1998), 63(15), 4996–5000.

Furthermore, optically active β-hydroxycarboxylic acid compounds represented by the formula (5) are transformed quantitatively into the optically active sulfonate compounds represented by the formula (1) by the reaction with sulfonylation agents in the presence of a base with high optical purity and these may be cheaply manufactured.

As sulfonylation agents, there may be mentioned sulfonic acid chlorides such as mesyl chloride, nosyl chloride, tosyl chloride, trifluoromethanesulfonyl chloride, trifluoromethylbenzenesulfonyl chloride, trifluoromethoxyl benzenesulfonyl chloride, bromobenzenesulfonyl chloride, dibromobenzenesulfonyl chloride, chlorobenzenesulfonyl chloride, dichlorobenzenesulfonyl chloride, trichlorobenzenesulfonyl chloride, fluorobenzenesulfonyl chloride, difluorobenzenesulfonyl chloride, trifluorobenzenesulfonyl chloride, cyanobenzenesulfonyl chloride, t-butylbenzenesulfonyl chloride, biphenylsulfonyl chloride, naphthalenesulfonyl chloride, triisopropylbenzenesulfonyl chloride, 2,4-dichloro-5-methylbenzenesulfonyl chloride, 2,5-dibromo-3,6-difluorobenzenesulfonyl chloride, mesitylenesulfonyl chloride, etc. and sulfonic acid anhydride like trifluoromethanesulfonic acid anhydride. Especially suitable are mesyl chloride, tosyl chloride, trifluoromethanesulfonyl chloride, trifluoromethanesulfonic acid anhydride and particularly preferred are trifluoromethanesulfonyl chloride and trifluoromethanesulfonic acid anhydride. In other words, according to the present invention, the optically active sulfonate compounds, in which $R^1$ in the above described formula (1) is a methyl group, p-tolyl group, or trifluoromethyl group, are suitably used, particularly optically active sulfonyl compounds with a trifluoromethyl group as $R^1$ are preferably used.

There is no special limitation on the amount of sulfonylation agent, but per mole of the optically active β-hydroxycarboxylic acid compound represented by the formula (5) preferably 1.0 to 2.0 equivalents, particularly preferred 1.0 to 1.1 equivalents of sulfonylation agent are used. Inorganic bases as well as organic bases may be used as bases. Among organic bases, tertiary amines are suitable and triethylamine, diisopropylethylamine, pyridine, DMAP (dimethylamino pyridine) etc. are used preferably. There is no special limitation on the amount of base, but per mole of the optically active β-hydroxycarboxylic acid compound represented by the formula (5) preferably 0.5 to 2.0 equivalents, particularly preferred in the range of 0.9 to 1.2 equivalents are used. As solvents, aprotic solvents are preferred and especially halogenated solvents like dichloromethane, ether type solvents such as THF (tetrahydrofuran), MTBE (methyl-t-butyl ether), ester type solvents such as ethyl acetate, isopropyl acetate, aromatic hydrocarbon type solvents such as toluene, xylene, polar solvents such as acetonitrile, dimethylformamide, dimethylacetoamide etc. are preferably used. At the beginning of the reaction, the concentration of the optically active β-hydroxycarboxylic acid compound is generally in a range of 0.001 to 10 mole/L, preferably it may be in a range of 0.02 to 0.5 mole/L. The reaction temperature is generally in a range of −78 to 40° C., preferably in a range of −40 to 25° C., but it is selected in terms of yield and economical efficiency. The reaction time differs depending on the other reaction conditions, but generally it is in an extent of several minutes to 24 hours, in terms of yield and economical efficiency, 30 minutes to 2 hours are preferred.

Subsequent to the sulfonylation reaction, the amination reaction (the reaction of the optically active sulfonate compounds represented by the formula (1) with the aromatic amines represented by the formula (2)) is carried out, and the optically active sulfonate compounds obtained by the sulfonylation reaction may be used after isolation from the reaction mixture, but generally the reaction mixture may be used as it is without further purification. This is significantly economical because of no loss of optically active sulfonate compounds. Additionally, it is possible to perform the sulfonylation reaction and the amination reaction successively in a same reactor without cleaning and drying.

The optically active sulfonate compounds represented by the formula (1) are transformed into the optically active N-aryl-β-amino acid compounds represented by the formula (3) by the reaction with the aromatic amines indicated by the formula (2).

There is no special limitation on the amount of aromatic amine, but per mole of the sulfonate compounds preferably 1.0 to 4.0 equivalents, more preferably 1.0 to 3.2, particularly preferred range of 2.0 to 2.2 equivalents may be used.

The reaction temperature for the amination is generally 5° C. or less, preferably 0° C. or less, preferably it is set to −10° C. or less. If the reaction temperature becomes too high, there is a tendency for the target compound to racemize. If the reaction temperature becomes too low, there is a tendency for the reaction rate to decline. Further, because excessive cooling is economically unacceptable, the lower limit is normally −100° C. or above, particularly preferred is −78° C. or above. Therefore, the preferred range of the reaction temperature may be for instance −100 to 5° C., more preferred −100 to 0° C., further preferred −78 to 0° C., particularly preferred −78 to −10° C. The reaction time differs depending on the other reaction conditions, but generally it is in the order of 1 to 120 hours, and in terms of yield and economical efficiency 2 to 24 hours are particularly preferred.

At the end of the reaction step, the addition of an acid to reaction solution is preferable in order to terminate the reaction completely. As the acid, organic acids are preferable. Among the organic acids, acetic acid and trifluoroacetic acid are preferable.

There is no special limitation on the isolation of the target compound from the reaction mixture, and known methods to persons skilled in the art, such as silica gel chromatography, solvent extraction, crystallization etc. may be suitably adopted.

EXAMPLES

In the following the content of the present invention is concretely explained by the working examples, but these working examples do not restrict the present invention in any way. Further, in the working examples the optical purity is determined by chiral HPLC method.

Example 1

To a solution of 348 mg (3.0 mmol) of methyl acetoacetate in 3.0 ml methanol, 0.8 mg (0.001 mmol) $RuCl_2$(R)-binap was added and stirred in an autoclave under a hydrogen pressure of 30 atm at 80° C. for 66 hours. After concentration and distillation, 325 mg (2.76 mmol, 97% ee) of methyl (R)-3-hydroxybutanoate was obtained. The condition of chiral HPLC is the following. Column, CHIRALPAK AS-H manufactured by Daicel Chemical Industries, Ltd.; Eluate, Hexane:2-propanol=95:5; flow rate, 0.8 mL/min; Wavelength of detection, 210 nm; Temperature, 25° C.; Retention time, 13 min (S) and 16 min (R).

A solution of 118 mg (1.0 mmol, 97% ee) of this methyl (R)-3-hydroxybutanoate and 0.11 ml (1.2 mmol) of pyridine in 2 ml of dichloromethane was cooled to 0° C. and a solution of 0.31 ml (1.1 mmol) trifluoromethanesulfonic acid anhydride in 2 ml of dichloromethane was added by dropping within 1 hour under stirring.

After cooling the mixture to −40° C., 0.18 ml (2.0 mmol) of aniline was added and stirred at −40° C. for 16 hours. By conventional isolation with silica gel chromatography, 156 mg (yield 81%, optical purity 89% ee) of methyl (R)-3-(phenylamino)butanoate was obtained. The $^1$H-NMR and $^{13}$C-NMR data were identical with those described in Synthesis, 2000, 6, 789 to 800. The condition of chiral HPLC is the following. Column, CHIRALPAK AS-H manufactured by Daicel Chemical Industries, Ltd.; Eluate, Hexane:2-propanol=95:5; flow rate, 0.8 mL/min; Wavelength of detection, 210 nm; Temperature, 25° C.; Retention time, 10 min (R) and 11 min (S).

Example 2

A solution of 248 mg (2.1 mmol, 97% ee) of this methyl (R)-3-hydroxybutanoate and 0.38 ml (2.2 mmol) of diisopropylamine in 2 ml of dichloromethane was cooled to −78° C. and a solution of 652 mg (2.3 mmol) trifluoromethanesulfonic acid anhydride in 2 ml of dichloromethane was added by dropping within 1 hour under stirring.

After cooling the mixture to −78° C., 0.57 ml (6.3 mmol) of aniline was added and stirred at −40° C. for 16 hours. After quenching with trifluoroacetic acid, the yield and optical purity of methyl (S)-3-(phenylamino)butanoate were determined by HPLC. (yield 94%, optical purity 95% ee) The $^1$H-NMR and $^{13}$C-NMR data were identical with those described in Synthesis, 2000, 6, 789 to 800.

Example 3

A solution of 244 mg (2.1 mmol, 97% ee) of this methyl (R)-3-hydroxybutanoate and 0.38 ml (2.2 mmol) of diisopropylamine in 2 ml of dichloromethane was cooled to −78° C. and a solution of 641 mg (2.3 mmol) trifluoromethanesulfonic acid anhydride in 2 ml of dichloromethane was added by dropping within 1 hour under stirring.

After cooling the mixture to −78° C., 0.76 ml (6.2 mmol) of p-methoxyaniline was added and stirred at −40° C. for 16 hours. After quenching with trifluoroacetic acid, the yield and optical purity of methyl (S)-3-(p-methoxyphenylamino)butanoate were determined by HPLC (yield 77%, optical purity 96% ee). The condition of chiral HPLC is the following. Column, CHIRALPAK AS-H manufactured by Daicel Chemical Industries, Ltd.; Eluate, Hexane:2-propanol=90:10; flow rate, 1.0 mL/min; Wavelength of detection, 210 nm; Temperature, 25° C.; Retention time, 16 min (R) and 19 min (S).

$^1$H-NMR (400 MHz, $CDCl_3$): δ 1.25 (d, J=6.4 Hz, 3H), 2.41 (dd, J=15.0, 6.8 Hz, 1H), 2.62 (dd, J=15.0, 5.3 Hz, 1H), 3.68 (s, 3H), 3.74 (s, 3H), 3.81–3.89 (m, 1H), 6.59–6.63 (m, 2H), 6.76–6.80 (m, 2H); $^{13}$C-NMR (100 MHz, $CDCl_3$): δ 21.03, 41.12, 47.67, 51.98, 56.15, 115.36, 115.94, 141.22, 152.90, 172.79; IR (neat) 3373, 2954, 1729, 1509, 1233, 820 $cm^{-1}$; ESIMS m/z: 224 (M+H); Elemental analysis: calcd. for $C_{12}H_{17}NO_3$: C, 64.55; H, 7.67; N, 6.27. found: C, 63.75; H, 7.62; N, 6.25; $[\alpha]^{23}_D$=+13.1° (c=0.84, $CH_2Cl_2$).

Example 4

A solution of 243 mg (2.1 mmol, 97% ee) of this methyl (R)-3-hydroxybutanoate and 0.38 ml (2.2 mmol) of diisopropylamine in 2 ml of dichloromethane was cooled to −78° C. and a solution of 639 mg (2.3 mmol) trifluoromethanesulfonic acid anhydride in 2 ml of dichloromethane was added by dropping within 1 hour under stirring.

After cooling the mixture to −78° C., 0.79 ml (6.2 mmol) of p-methoxyaniline was added and stirred at −40° C. for 16 hours. After quenching with trifluoroacetic acid, the yield and optical purity of methyl (S)-3-(p-chlorophenylamino)butanoate were determined by HPLC (yield 72%, optical purity 82% ee). The condition of chiral HPLC is the following. Column, CHIRALPAK AS-H manufactured by Daicel Chemical Industries, Ltd.; Eluate, Hexane:2-propanol=95:5; flow rate, 1.0 mL/min; Wavelength of detection, 210 nm; Temperature, 25° C.; Retention time, 10 min (R) and 11 min (S).

$^1$H-NMR (400 MHz, $CDCl_3$): δ 1.26 (d, J=6.5 Hz, 3H), 2.44 (dd, J=15.0, 6.7 Hz, 1H), 2.60 (dd, J=15.0, 5.3 Hz, 1H), 3.68 (s, 3H), 3.85–3.92 (m, 1H), 6.52–6.56 (m, 2H), 7.09–7.13 (m, 2H); $^{13}$C-NMR (100 MHz, $CDCl_3$): δ 20.88, 40.94, 46.60, 52.07, 115.10, 122.66, 129.58, 145.73, 172.49; IR (neat) 3390, 2970, 1727, 1600, 1497, 1293, 1177, 816 $cm^{-1}$; ESIMS m/z: 228 (M+H); Elemental analysis: calcd. for $C_{11}H_{14}ClNO_2$: C, 58.03; H, 6.20; N, 6.15. found: C, 58.20; H, 6.19; N, 6.05; $[\alpha]^{23}_D$=+7.230 (c=1.3, $CH_2Cl_2$).

Example 5

To a solution of 6.22 mg (48 mmol) of methyl 3-ketovalerate in 48 ml methanol, 36 mg (0.004 mmol) $RuCl_2$(S)-binap was added and stirred in an autoclave under a hydrogen pressure of 30 atm at 80° C. for 66 hours. After concentration and distillation, 5.71 g (43.2 mmol, 97% ee) of methyl (S)-3-hydroxyvalerate was obtained. The condition of chiral HPLC is the following. Column, CHIRALPAK OD manufactured by Daicel Chemical Industries, Ltd.; Eluate, Hexane:2-propanol=95:5; flow rate, 1.0 mL/min; Wavelength of detection, 210 nm; Temperature, 25° C.; Retention time, 15 min (R) and 27 min (S).

A solution of 270 mg (2.0 mmol, 97% ee) of this methyl (S)-3-hydroxybutanoate and 0.38 ml (2.2 mmol) of diisopropylamine in 2 ml of dichloromethane was cooled to −78° C. and a solution of 634 mg (2.3 mmol) trifluoromethanesulfonic acid anhydride in 2 ml of dichloromethane was added by dropping within 1 hour under stirring.

After cooling the mixture to −78° C., 0.56 ml (6.1 mmol) of aniline was added and stirred at −40° C. for 16 hours. After quenching with trifluoroacetic acid, the yield and optical purity of methyl (R)-3-(phenylamino)valerate were determined by HPLC (yield 85%, optical purity 97% ee). The condition of chiral HPLC is the following. Column, CHIRALPAK AS-H manufactured by Daicel Chemical Industries, Ltd.; Eluate, Hexane:2-propanol=95:5; flow rate, 1.0 mL/min; Wavelength of detection, 210 nm; Temperature, 25° C.; Retention time, 6.1 min (R) and 6.8 min (S).

$^1$H-NMR (400 MHz, CDCl$_3$): δ0.98 (t, J=7.4 Hz, 3H), 1.54–1.70 (m, 2H), 2.49 (dd, J=15.0, 6.3 Hz, 1H), 2.58 (dd, J=15.0, 5.7 Hz, 1H), 3.66 (s, 3H), 3.72–3.78 (m, 1H), 6.61–6.64 (m, 2H), 6.67–6.71 (m, 1H), 7.14–7.19 (m, 2H); $^{13}$C-NMR (100 MHz, CDCl$_3$): δ 10.88, 28.14, 39.12, 52.00, 52.23, 113.89, 117.92, 129.74, 147.57, 172.83; IR (neat) 3390, 2970, 1729, 1602, 1507 cm$^{-1}$; ESIMS m/z: 208 (M+H); Elemental analysis: calcd. for C$_{12}$H$_{17}$NO$_2$: C, 69.54; H, 8.27; N, 6.76. found: C, 69.48; H, 8.31; N, 6.50; [α]$^{23}_D$=+27.6° (c=2.1CH$_2$Cl$_2$).

Example 6

To a solution of 2.88 g (20 mmol) of methyl 3-ketohexanoate in 10 ml methanol, 36 mg (0.004 mmol) RuCl$_2$(R)-binap was added and stirred in an autoclave under a hydrogen pressure of 100 atm at 30° C. for 66 hours. After concentration and distillation, 2.24 g (15.4 mmol, 99% ee) of methyl (S)-3-hydroxyhexanoate was obtained. The condition of chiral HPLC is the following. Column, CHIRALPAK OD-H manufactured by Daicel Chemical Industries, Ltd.; Eluate, Hexane:2-propanol=90:10; flow rate, 1.0 mL/min; Wavelength of detection, 210 nm; Temperature, 25° C.; Retention time, 5 min (R) and 7 min (S).

A solution of 248 mg (1.7 mmol, 99% ee) of this methyl (S)-3-hydroxyhexanoate and 0.31 ml (1.7 mmol) of diisopropylamine in 2 ml of dichloromethane was cooled to −78° C. and a solution of 527 mg (1.9 mmol) trifluoromethanesulfonic acid anhydride in 2 ml of dichloromethane was added by dropping within 1 hour under stirring.

After cooling the mixture to −78° C., 0.46 ml (5.1 mmol) of aniline was added and stirred at −40° C. for 16 hours. After quenching with trifluoroacetic acid, the yield and optical purity of methyl (S)-3-(phenylamino)hexanoate were determined by HPLC (yield 94%, optical purity 96% ee). The condition of chiral HPLC is the following. Column, CHIRALPAK AS-H manufactured by Daicel Chemical Industries, Ltd.; Eluate, Hexane:2-propanol=99:1; flow rate, 1.0 mL/min; Wavelength of detection, 210 nm; Temperature, 25° C.; Retention time, 9 min (R) and 10 min (S).

$^1$H-NMR (400 MHz, CDCl$_3$): δ 0.918 (t, J=7.2 Hz, 3H), 1.35–1.58 (m, 4H), 2.48 (dd, J=15.1, 6.4 Hz, 1H), 2.57 (dd, J=15.1, 5.6 Hz, 1H), 3.65 (s, 3H), 3.70–3.84 (m, 1H), 6.60–6.62 (m, 2H), 6.66–6.70 (m, 1H), 7.14–7.18 (m, 2H); $^{13}$C-NMR (100 MHz, CDCl$_3$): δ 14.37, 19.76, 37.70, 39.56, 50.57, 52.01, 113.83, 117.88, 129.76, 147.62, 172.93; IR (neat) 3386, 2958, 1729, 1602, 1175, 747 cm$^{-1}$; ESIMS m/z: 224 (M+H); Elemental analysis: calcd. for C$_{12}$H$_{17}$NO$_3$: C, 64.55; H, 7.67; N, 6.27. found: C, 63.75; H, 7.62; N, 6.25; [α]$^{23}_D$=−31.1° (c=0.53, CH$_2$Cl$_2$).

Example 7

To a solution of 2.88 g (20 mmol) of methyl 3-keto-4-methylvarelate in 10 ml methanol, 36 mg (0.004 mmol) RuCl$_2$(R)-binap was added and stirred in an autoclave under a hydrogen pressure of 100 atm at 30° C. for 66 hours. After concentration and distillation, 2.54 g (1.7.4 mmol, 98% ee) of methyl (S)-3-hydroxy-4-methylvalerate was obtained. The condition of chiral HPLC is the following. Column, CHIRALPAK OD-H manufactured by Daicel Chemical Industries, Ltd.; Eluate, Hexane:2-propanol=90:10; flow rate, 1.0 mL/min; Wavelength of detection, 210 nm; Temperature, 25° C.; Retention time, 5 min (S) and 7 min (R).

A solution of 245 mg (1.7 mmol, 98% ee) of this methyl (S)-3-hydroxy-4-methylvalerate and 0.28 ml (1.6 mmol) of diisopropylamine in 2 ml of dichloromethane was cooled to −78° C. and a solution of 474 mg (1.7 mmol) trifluoromethanesulfonic acid anhydride in 2 ml of dichloromethane was added by dropping within 1 hour under stirring.

After cooling the mixture to −78° C., 0.42 ml (4.6 mmol) of aniline was added and stirred at −40° C. for 16 hours. After quenching with trifluoroacetic acid, the yield and optical purity of methyl (R)-3-(phenylamino)-4-methylvalerate were determined by HPLC (yield 21%, optical purity 98% ee). The condition of chiral HPLC is the following. Column, CHIRALPAK AS-H manufactured by Daicel Chemical Industries, Ltd.; Eluate, Hexane:2-propanol=99:1; flow rate, 1.0 mL/min; Wavelength of detection, 210 nm; Temperature, 25° C.; Retention time, 8 min (S) and 9 min (R).

$^1$H-NMR (400 MHz, CDCl$_3$): δ 0.978 (d, J=4.0 Hz, 3H), 1.00 (d, J=4.0 Hz, 3H), 1.88–1.96 (m, 1H), 2.46 (dd, J=14.9, 7.2 Hz, 1H), 2.54 (dd, J=14.9, 5.6 Hz, 1H), 3.62 (s, 3H), 3.68–3.74 (m, 1H), 6.60–6.64 (m, 2H), 6.65–6.69 (m, 1H), 7.13–7.17 (m, 2H); $^{13}$C-NMR (100 MHz, CDCl$_3$): δ 18.92, 32.07, 37.22, 52.25, 56.31, 113.92, 117.83, 129.72, 147.93, 173.86; IR (neat) 3197, 2960, 1710, 1602, 1194, 749 cm$^{-1}$; ESIMS m/z: 224 (M+H); Elemental analysis: calcd. for C$_{12}$H$_{17}$NO$_3$: C, 64.55; H, 7.67; N, 6.27. found: C, 63.75; H, 7.62; N, 6.25; [α]$^{23}_D$=−27.210 (c=0.73, CH$_2$Cl$_2$).

Reference Example

To a solution of 348 mg (3.0 mmol) of commercially available methyl acetoacetate in 3.0 ml of methanol, 0.8 mg (0.001 mmol) RuCl$_2$(R)-binap was added and stirred in an autoclave under a hydrogen pressure of 30 atm at 80° C. for 66 hours. After concentration and distillation, 325 mg (2.76 mmol, 97% ee) of methyl (R)-3-hydroxybutanoate was obtained. The condition of chiral HPLC is the following. Column, CHIRALPAK AS-H manufactured by Daicel Chemical Industries, Ltd.; Eluate, Hexane:2-propanol=95:5; flow rate, 0.8 mL/min; Wavelength of detection, 210 nm; Temperature, 25° C.; Retention time, 13 min (S) and 16 min (R).

A solution of 118 mg (1.0 mmol, 97% ee) of this methyl (R)-3-hydroxybutanoate and 0.11 ml (1.2 mmol) of pyridine in 2 ml of dichloromethane was cooled to 0° C. and a solution of 0.31 ml (1.1 mmol) of trifluoromethanesulfonic acid anhydride in 2 ml of dichloromethane was added by dropping within 1 hour under stirring.

After warming the mixture to 25° C., 0.18 ml (2.0 mmol) of aniline was added to the mixture and stirred at 25° C. for 16 hours. By conventional isolation with silica gel chromatography, 170 mg (yield 88%, optical purity 19% ee) of the target compound methyl (S)-3-(phenylamino)butanoate was obtained. The condition of chiral HPLC is the following. Column, CHIRALPAK AS-H manufactured by Daicel Chemical Industries, Ltd.; Eluate, Hexane:2-propanol=95:5; flow rate, 0.8 mL/min; Wavelength of detection, 210 nm; Temperature, 25° C.; Retention time, 10 min (R) and 11 min (S).

[Advantages of the Invention]

According to the method of the present invention, optically active N-aryl-β-amino acid compounds, which are useful as intermediate compounds for pharmaceuticals and agrochemicals, can be obtained in high yield with high optical purity. A production method suitable for the commercial manufacture of optically active N-aryl-β-amino acid compounds is offered. Further, by the production method according to the present invention, they can be manufactured from cheaply available β-keto carboxylic acid compounds as starting materials with a relatively low number of operations. Moreover, it is a superior method inasmuch as optically active N-aryl-β-amino acid compounds of the desired configuration can be manufactured.

What is claimed is:

1. A method of producing an optically active N-aryl-β-amino acid compound comprising reacting an optically active sulfonate compound represented by the formula (1):

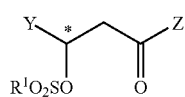

wherein

Y is an optionally substituted methyl group or aryl group,

Z is a hydroxy group, optionally substituted amino group, optionally substituted alkoxy group or optionally substituted aryloxy group, $R^1$ is an optionally substituted alkyl group with a carbon atom number from 1 to 10, an optionally substituted aryl group with a carbon atom number from 6 to 15, an optionally substituted aralkyl group with a carbon atom number from 7 to 20, and

* indicates an chiral carbon atom, in the R or S configuration;

with an aromatic amine represented by formula (2):

X—NH$_2$     (2)

wherein

X is an optionally substituted aryl group with a carbon atom number from 6 to 15 or an optionally substituted heteroaromatic group with a carbon atom number from 3 to 15;

to produce said optically active N-aryl-β-amino acid compound, wherein said optically active N-aryl-β-amino acid compound is represented by formula (3):

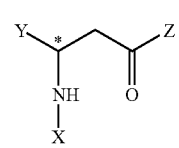

wherein X, Y, Z and * are as defined above.

2. The method as claimed in claim 1 further comprising a producing a compound of formula (1) by reacting an optically active β-hydroxycarboxylic acid compound represented by formula (5):

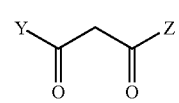

wherein Y, Z and * are as defined in claim 1;
with sulfonyl chlorides or sulfonic acid anhydride.

3. The method as claimed in claim 2 further comprising producing a compound of formula (5) by contacting an asymmetric reduction of a β-keto carboxylic acid compound represented by formula (4)

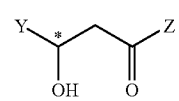

wherein Y and Z are as defined in claim 2;
with a catalyst or enzyme.

4. The method as claimed in claim 1, wherein $R^1$ in the sulfonate compound of formula (1) is a trifluoromethyl, methyl or p-tolyl group.

5. The method as claimed in claim 4, wherein $R^1$ in the sulfonate compound of formula (1) is trifluoromethyl.

6. The method as claimed in claim 1, wherein in the sulfonate compound of formula (1) the sulfonyl group is introduced by using trifluoromethanesulfonic acid anhydride as a sulfonylation agent and $R^1$ is a trifluoromethyl group.

7. The method as claimed in claim 1, wherein said reacting is at a temperature of 5° C. or less.

8. The method as claimed in claim 2, wherein $R^1$ in the sulfonate compound of formula (1) is a trifluoromethyl, methyl or p-tolyl group.

9. The method as claimed in claim 8, wherein $R^1$ in the sulfonate compound of formula (1) is trifluoromethyl.

10. The method as claimed in claim 2, wherein in the sulfonate compound of formula (1) the sulfonyl group is introduced by using trifluoromethanesulfonic acid anhydride as a sulfonylation agent and $R^1$ is a trifluoromethyl group.

11. The method as claimed in claim 2, wherein said reacting is at a temperature of 5° C. or less.

12. The method as claimed in claim 3, wherein $R^1$ in the sulfonate compound of formula (1) is a trifluoromethyl, methyl or p-tolyl group.

13. The method as claimed in claim 12, wherein $R^1$ in the sulfonate compound of formula (1) is trifluoromethyl.

14. The method as claimed in claim 3, wherein in the sulfonate compound of formula (1) the sulfonyl group is introduced by using trifluoromethanesulfonic acid anhydride as a sulfonylation agent and $R^1$ is a trifluoromethyl group.

15. The method as claimed in claim 3, wherein said reacting is at a temperature of 5° C. or less.

16. The method as claimed in claim 3, wherein said catalyst is a Ru-binap catalyst.

17. The method of claim 1, wherein an optically active β-hydroxycarboxylic acid compound represented by formula (5):

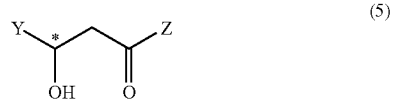

(5)

wherein Y, Z and * are as defined in claim 1;

is reacted with a sulfonylating reagent in the presence of an organic teritiary amine to produce said optically active sulfonate compound represented by the formula (1).

18. The method of claim 17, wherein said optically active sulfonate compound represented by the formula (1) is reacted with said aromatic amine represented by formula (2) without isolation from the reaction mixture.

* * * * *